US00PP33186P2

(12) United States Plant Patent
Van Swieten

(10) Patent No.: US PP33,186 P2
(45) Date of Patent: Jun. 22, 2021

(54) ***PHALAENOPSIS* ORCHID PLANT NAMED 'PHALKEDHY'**

(50) Latin Name: ***Phalaenopsis* hybrid**
Varietal Denomination: PHALKEDHY

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 16/974,258

(22) Filed: Dec. 2, 2020

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — Jondle & Associates, P.C.

(57) ABSTRACT

A new and distinct variety of *Phalaenopsis* plant named 'PHALKEDHY', particularly characterized by reddish-purple flowers with dark red-purple lips, a concave flower shape in lateral view, dark red whiskers with light yellow tips, and is propagated by meristem tissue culture, is disclosed.

3 Drawing Sheets

Genus and species: *Phalaenopsis* hybrid.
Variety denomination: 'PHALKEDHY'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALKEDHY'.

The new *Phalaenopsis* plant is a product of a planned breeding program conducted by the inventor in Bleiswijk, the Netherlands. The objective of this breeding program was to create a new *Phalaenopsis* plant with reddish-purple flowers and dark red-purple lips, suitable for potted plant production.

The new *Phalaenopsis* plant 'PHALKEDHY' is a result of cross-pollination made by the inventor in January 2012 in Bleiswijk, the Netherlands, of the proprietary female, or seed parent, *Phalaenopsis* hybrid 'PHALDRIBIP' (U.S. Plant Pat. No. 26,960) with the proprietary male, or pollen parent, *Phalaenopsis* hybrid 'PHALDANBO' (U.S. Plant Pat. No. 25,930).

The new *Phalaenopsis* was selected by the inventor as a single plant within the progeny of the stated cross-pollination in a controlled greenhouse in Bleiswijk, the Netherlands, in January 2015. Asexual reproduction of the new *Phalaenopsis* plant by meristem tissue culture since 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Jan. 30, 2020 (Application no. 2020/0288), by Applicant who obtained the subject matter disclosed directly from the inventor. 'PHALKEDHY' has not been made publicly available or sold anywhere in the world prior to the effective filing date of this application with the exception of sales or disclosures made one year or less before the effective filing date of this claimed invention by Applicant who obtained 'PHALKEDHY' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALKEDHY' as a new and distinct variety of *Phalaenopsis* plant:

1) Reddish-purple flowers with dark red-purple lips;
2) Flower shape in lateral view is concave; and
3) Dark red whiskers with light yellow tips.

DESCRIPTION OF THE PHOTOGRAPHS

This new *Phalaenopsis* plant is illustrated by the accompanying photographs which show the overall plant habit including blooms, bud, and foliage of the plant; the colors shown are as true as can be reasonably obtained by conventional photographic procedures. The photographs were taken in a greenhouse in Bleiswijk, the Netherlands, from 50-week-old plants in November 2020. Colors in the photographs may differ from the color values cited in the detailed botanical description, which accurately describe the actual colors of the new variety.

DESCRIPTION OF THE NEW VARIETY

Figure 1:
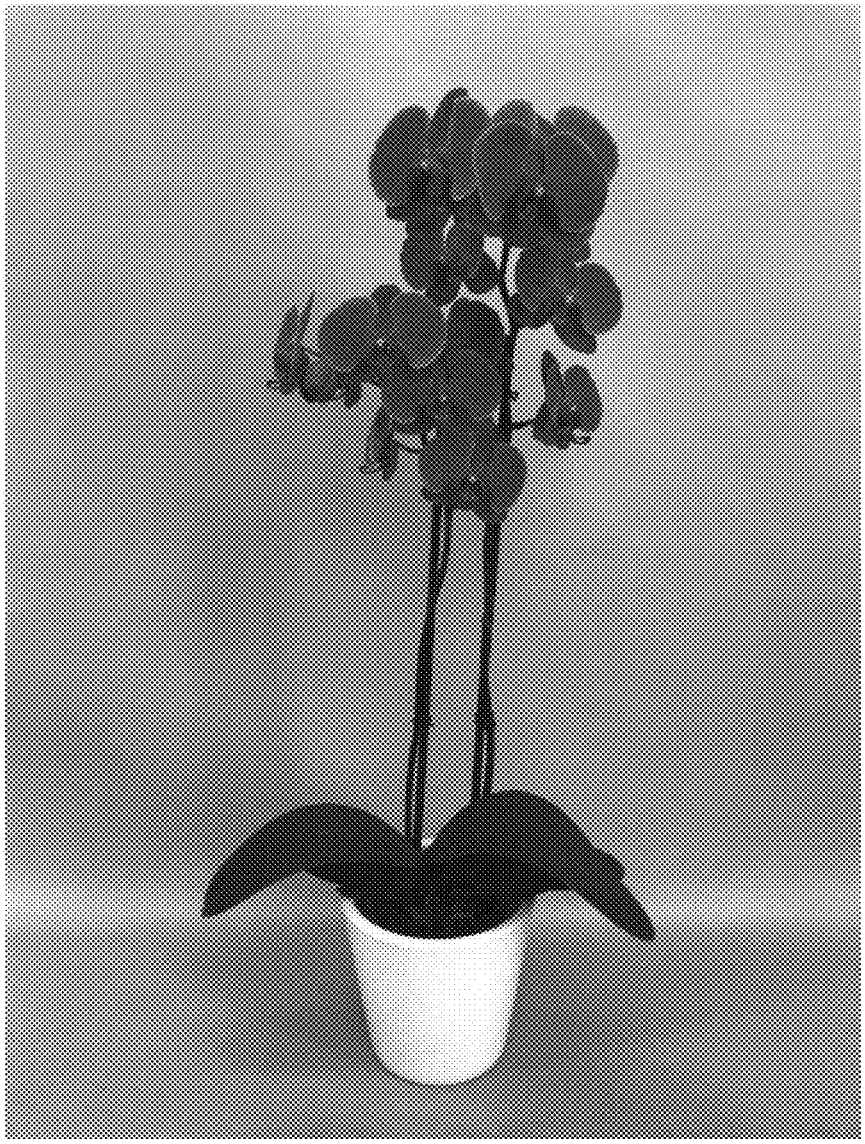
FIG. 1 shows the overall plant habit, including blooms, bud, and foliage of 'PHALKEDHY'.
Figure 2:
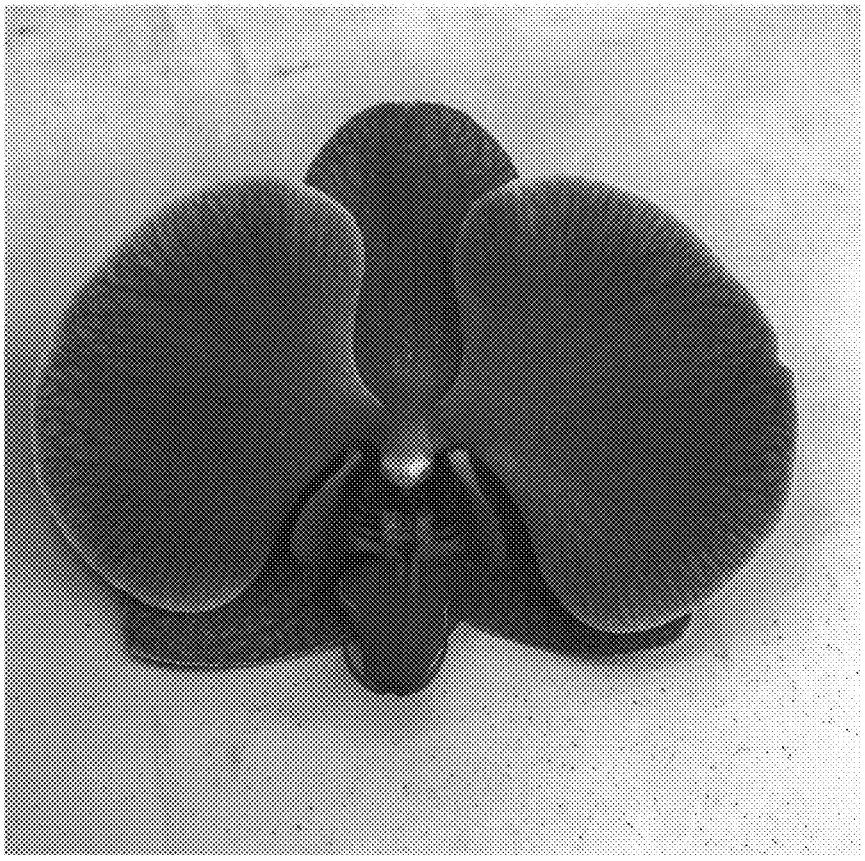
FIG. 2 shows a close-up of a flower of 'PHALKEDHY'.
Figure 3:
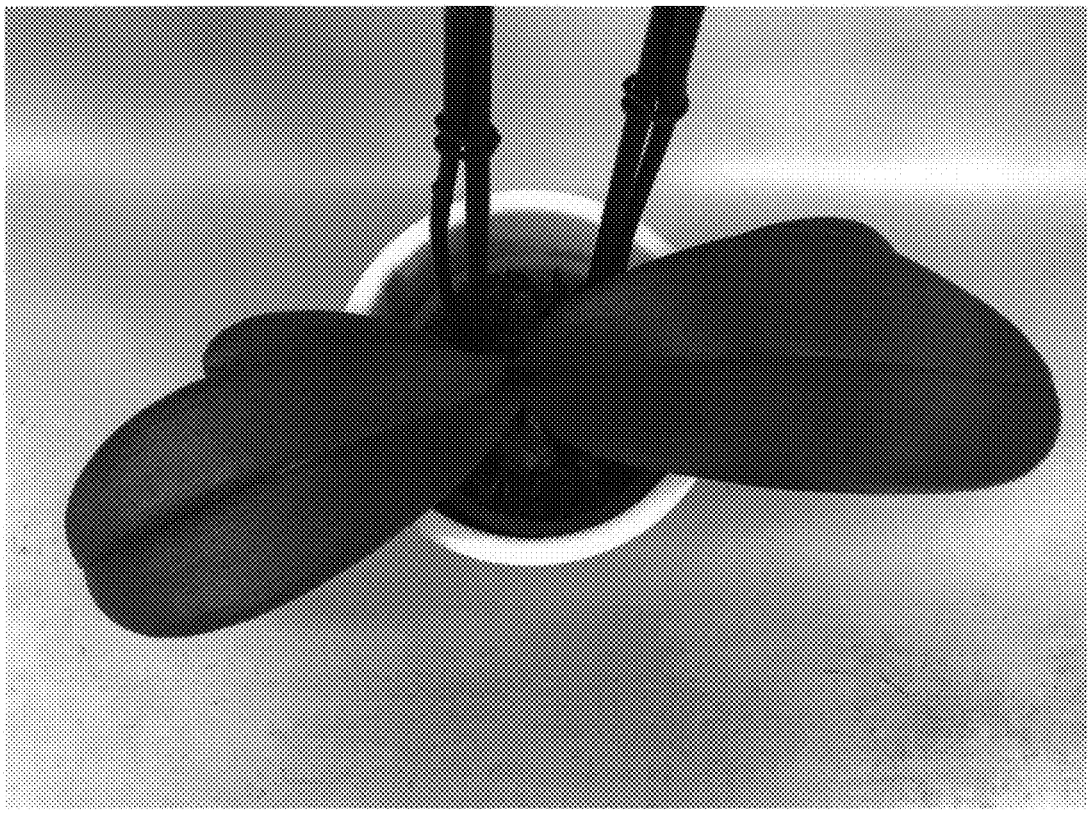
FIG. 3 shows an overhead view of the leaves of 'PHALKEDHY'.

The following detailed description sets forth the distinctive characteristics of 'PHALKEDHY'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in November 2020 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALKEDHY'.

Parentage:

*Female parent*.—*Phalaenopsis* cultivar 'PHALDRIBIP' (U.S. Plant Pat. No. 26,960).

*Male parent*.—*Phalaenopsis* cultivar 'PHALDANBO' (U.S. Plant Pat. No. 25,930).

Propagation:

*Type*.—Meristem tissue culture.

Roots:

*Root description*.—Greyed-green (something between RHS 190B and 190C) colored roots with branching lateral roots having yellow-green (RHS 146B) with a hint of purple-red (something in between RHS N77A and N77B) colored root tips.

Plant:

*Commercial crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme inflorescence.

*Height* (*from soil level to top of inflorescence*).—Approximately 48.0 cm to 58.0 cm.

*Width* (*measured from leaf tips*).—About 37.0 cm to 39.0 cm.

*Vigor*.—Strong.

Leaves:

*Mature leaves*.—Quantity per plant: 7 to 8 leaves are produced before flowering. Length (fully expanded): 19.0 cm to 22.0 cm. Width: 7.5 cm to 8.5 cm. Position of the broadest part of the leaf: At the middle. Shape: Oblong. Base shape: Moderately elongated. Apex: Unequal obtuse. Leaf blade angle with the petiole (measured from the horizontal position): Between 10 degrees and 30 degrees. Leaf margin: Entire. Color: Upper surface: Something in between RHS 147A and 146A. Lower surface: RHS 146B and diluting purple (RHS N77A) toward margins. Texture (both upper and lower surfaces): Smooth. Thickness: 2.1 mm to 2.4 mm. Variegation: Absent. Venation: Pattern: Parallel. Color of the midvein: Upper surface: RHS 147A. Lower surface: RHS N77A.

Peduncle:

*Quantity per plant*.—1 to 2.

*Number of flowers per peduncle*.—7 to 9.

*Length*.—48.0 cm to 58.0 cm.

*Diameter*.—5.0 mm to 6.0 mm.

*Strength*.—Strong.

*Aspect*.—Upright to slightly pendent.

*Texture*.—Smooth.

*Color*.—Brown (RHS 200B) with a touch of yellow-green (RHS 146C).

*Internode length*.—4.0 cm to 5.0 cm.

Inflorescence description:

*Appearance*.—Upright to slightly pendent, raceme inflorescence with bilaterally symmetrical flowers that open in succession beginning with the lowermost flower.

*Number of inflorescences*.—1 to 2.

*Inflorescence size*.—Height (from base to tip): 200.0 mm to 250.0 mm.

*Flowering time*.—First flowers can be expected 10 to 11 months after planting in a 12-cm pot.

*Flower*.—Height: 68.0 mm to 73.0 mm. Diameter: 85.0 mm to 90.0 mm. Depth of lip: 24.0 mm to 26.0 mm.

*Flower longevity*.—On the plant: 11 to 13 weeks.

*Flower shape in lateral view*.—Concave.

*Fragrance*.—Absent.

*Flower bud*.—Average size: Large. Length: 23.0 mm to 25.0 mm. Width: 20 0 mm to 22.0 mm. Shape: Egg shaped. Color: Yellow-green (RHS 146D) at the base with a hint of dark purplish-red (RHS N79C).

*Petals*.—Arrangement: Open/free. Shape: Semi-circular. Apex: Emarginated asymmetric. Margin: Weakly undulated. Length (from base to tip): 40.0 mm to 42.0 mm. Width: 53.0 mm to 55.0 mm. Position of the broadest part of the petal: Toward the base. Color (when fully opened): Upper surface: Basic color: Reddish-purple (RHS N78A). Over color: Stripes (something in between RHS N78A and N79C) and small light purple edge (RHS 76A). Lower surface: Basic color: Purplish-pink (RHS N78C). Over color: Light reddish-purple (RHS N78D) toward margin. Number of spots and stripes on the petals (upper surface): Many stripes. Color of spots and stripes on the petals (upper surface): Something in between RHS N78A and N79C. Density of netting of the petals (upper surface): None. Color of the netting (upper surface): Not applicable.

*Dorsal sepal*.—Shape: Elliptic. Apex: Rounded symmetric. Margin: Entire. Length (from base to tip): 41.0 mm to 43.0 mm. Width: 31.0 mm to 33.0 mm. Position of the broadest part of the dorsal sepals: At the middle. Color (when fully opened): Upper surface: Basic color: Reddish-purple (RHS N78A). Over color: Absent. Lower surface:. Basic color: Purplish-pink (RHS N78C). Over color: Light yellow-green (RHS 145C). Number of spots and stripes on the dorsal sepals (upper surface): Medium stripes. Color of spots and stripes on the dorsal sepals (upper surface): RHS N79C. Density of netting of the dorsal sepals (upper surface): Medium.. Color of the netting: RHS N79C.

*Lateral sepals*.—Shape: Ovate. Apex: Obtuse symmetric. Margin: Entire. Length (from base to tip): 39.0 mm to 41.0 mm. Width: 29.0 mm to 31.0 mm. Position of the broadest part of the lateral sepals: At the base. Color (when fully opened): Upper surface: Basic color: Reddish-purple (RHS N78C). Over color: Hint of light yellow-green (RHS 145C) at the base. Lower surface: Basic color: Red-purple (something in between RHS N78B and N78C). Over color: Light yellow-green (RHS 145C) and reddish-purple midvein (RHS N78A) toward the tip. Number of spots, dots, and stripes on the lateral sepals (upper surface): Few small dots at the base; medium stripes. Color of spots, dots, and stripes on the lateral sepals (upper surface): Dots (RHS 59A); stripes (RHS N79C). Density of netting of the lateral sepals (upper surface): Medium. Color of the netting (upper surface): RHS N79C.

*Labellum* (*lip*).—Whiskers: Present. Length of whiskers: 17.0 mm to 19 0 mm. Color of whiskers: Dark red (RHS 59A) with light yellow tips (RHS 10B). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Entire. Length: 19.0 mm to 21.0 mm. Width: 13.0 mm to 15.0 mm. Color: Upper surface: Yellow (RHS 13B) striped (RHS 183A) at the base; dark red (RHS 59A) and reddish-purple (RHS N78A) toward margin. Lower surface: Hint of yellow-green (RHS 195B) at the base; dark red (RHS 59A) on sides toward base and reddish-purple (RHS N78B) toward the tip. Number of spots and stripes on the lateral lobe: Few stripes at the base. Color of spots and stripes on the lateral lobe: RHS 183A. Density of netting of the lateral lobe: None. Color of the netting: Not applicable.

*Apical lobe*.—Shape: Triangular. Margin: Entire. Length: 20.0 mm to 22.0 mm. Width: 17.0 mm to 19.0 mm. Color: Upper surface: Hint of yellow (RHS 15B) at the base; dark red (RHS 59A) and dark purplish-red (RHS N79C) toward whiskers. Lower surface: Dark red wings (RHS 59A); red-purple (something in between RHS N78A and N79C) at the middle from base toward whiskers. Number of spots and stripes on the apical lobe: None. Color of spots and stripes on the apical lobe: Not applicable. Density of netting of the apical lobe: None. Color of the netting: Not applicable.

*Callus*.—Average size: Medium. Height: 5.0 mm to 6.0 mm. Length: 5.0 mm to 6.0 mm. Width: 3.0 mm to 4.0 mm. Color: Yellow (RHS 15B); dotted (RHS 178A).

Reproductive organs:

*Column*.—Length: 8.0 mm to 10.0 mm. Diameter: 5.0 mm to 6.0 mm. Color: Reddish-purple (RHS N78B).

*Pollinia*.—Quantity: 2. Diameter: 0.9 mm to 1.1 mm. Color: Orange (RHS 24A).

*Ovary*.—Length: 9.0 mm to 11.0 mm. Diameter: 2.2 mm to 2.5 mm.

*Pedicel*.—Length: 31.0 mm to 33.0 mm. Diameter: 2.7 mm to 3.0 mm. Texture: Smooth. Color: Reddish-brown (RHS 176B) at the base; light yellow-green (RHS 195B) with a hint of light purple (RHS 76A) toward flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALKEDHY' differs from the female parent plant 'PHALDRIBIP' (U.S. Plant Pat. No. 26,960), in that 'PHALKEDHY' has dark red whiskers with light yellow tips, whereas 'PHALDRIBIP' has red-purple whiskers. Additionally, 'PHALKEDHY' has longer whiskers than 'PHALDRIBIP'.

'PHALKEDHY' differs from the male parent plant 'PHALDANBO' (U.S. Plant Pat. No. 25,930) in that 'PHALKEDHY' has emarginate petal apexes, triangular apical lobes, and dark red whiskers with light yellow tips, whereas 'PHALDANBO' has mucronate petal apexes, obdeltoid apical lobes, and dark red-purple whiskers.

'PHALKEDHY' is most similar to the commercial *Phalaenopsis* plants named 'PHALDUKAI' (U.S. Plant Pat. No. 28,157) and 'PHALGLAOR' (U.S. Plant Pat. No. 31,482). 'PHALKEDHY' differs from the commercial variety 'PHALDUKAI' in that 'PHALKEDHY' has medium-sized calluses, whereas 'PHALDUKAI' has large-sized calluses. Additionally, 'PHALKEDHY' has narrower dorsal sepals and narrower leaves than 'PHALDUKAI'.

'PHALKEDHY' differs from the commercial variety 'PHALGLAOR' in that 'PHALKEDHY' has emarginate petal apexes and medium-sized calluses, whereas 'PHALGLAOR' has rounded to slightly mucronate petal apexes and medium- to large-sized calluses.

I claim:

1. A new and distinct variety of *Phalaenopsis* plant named 'PHALKEDHY', substantially as described and illustrated herein.

* * * * *